(12) United States Patent
Khosroshahi et al.

(10) Patent No.: US 12,318,490 B2
(45) Date of Patent: Jun. 3, 2025

(54) METHOD FOR FABRICATION OF NANOSTRUCTURE

(71) Applicant: M.I.S. Electronics Inc., Richmond Hill (CA)

(72) Inventors: Mohammad E Khosroshahi, Richmond Hill (CA); Vaughn Woll-Morison, Richmond Hill (CA); Tiam Mohmedi, Richmond Hill (CA)

(73) Assignee: M.I.S. ELECTRONICS INC., Richmond Hill (CA)

( * ) Notice: Subject to any disclaimer, the term of this patent is extended or adjusted under 35 U.S.C. 154(b) by 897 days.

(21) Appl. No.: 17/233,469

(22) Filed: Apr. 17, 2021

(65) Prior Publication Data

US 2022/0117905 A1  Apr. 21, 2022

Related U.S. Application Data

(60) Provisional application No. 63/093,053, filed on Oct. 16, 2020.

(51) Int. Cl.
| | | |
|---|---|---|
| A61K 9/51 | (2006.01) | |
| A61K 47/46 | (2006.01) | |
| A61K 49/00 | (2006.01) | |
| C12N 1/14 | (2006.01) | |
| B82Y 5/00 | (2011.01) | |
| B82Y 25/00 | (2011.01) | |
| B82Y 30/00 | (2011.01) | |
| B82Y 35/00 | (2011.01) | |
| B82Y 40/00 | (2011.01) | |
| H01F 1/00 | (2006.01) | |

(52) U.S. Cl.
CPC .......... *A61K 9/5176* (2013.01); *A61K 9/5115* (2013.01); *A61K 47/46* (2013.01); *A61K 49/0043* (2013.01); *A61K 49/005* (2013.01); *C12N 1/14* (2013.01); *B82Y 5/00* (2013.01); *B82Y 25/00* (2013.01); *B82Y 30/00* (2013.01); *B82Y 35/00* (2013.01); *B82Y 40/00* (2013.01); *C12N 2500/24* (2013.01); *H01F 1/0054* (2013.01)

(58) Field of Classification Search
None
See application file for complete search history.

(56) References Cited

U.S. PATENT DOCUMENTS

| | | |
|---|---|---|
| 2006/0045809 A1 | 3/2006 | Shirai et al. |
| 2013/0260479 A1 | 10/2013 | Chou et al. |
| 2014/0200240 A1 | 7/2014 | Gabriel |

OTHER PUBLICATIONS

Mukherjee et al. Fungus-Mediated Synthesis of Silver Nanoparticles and Their Immobilization in the Mycelial Matrix: A Novel Biological Approach to Nanoparticle Synthesis. 2001 Nano Letters 1: 515-519. (Year: 2001).*

* cited by examiner

*Primary Examiner* — Jennifer Chin
(74) *Attorney, Agent, or Firm* — Jenna L. Wilson; Wilson Lue LLP

(57) ABSTRACT

A method for fabricating a nanostructure comprises adding a fungal mycelium (114) in a growth vessel (110). The growth vessel (110) comprising a growth medium (118). In the next step, the nanostructure is added in the growth vessel (110) which is then absorbed by the fungal mycelium (114) and finally distributed throughout the fungal mycelium (114). Further, a delivery vehicle for payload (206) is also disclosed which comprises the fabricated nanostructure.

15 Claims, 2 Drawing Sheets

METHOD FOR FABRICATION OF NANOSTRUCTURE

BACKGROUND

Unless otherwise indicated herein, the materials described in this section are not prior art in this application and are not admitted to being prior art by inclusion in this section.

Field

The subject described herein, in general, relates to biomedical engineering. More particularly, but not exclusively, the subject matter relates to a process for fabricating a nanostructure within a fungal mycelium.

Discussion of the Related Art

Medical imaging plays a crucial role in the diagnosis and treatment of diseases. Imaging modalities are employed to visualize tissue at cellular and molecular levels including nuclear imaging (positron emission tomography), single photon emission computed tomography, x-ray computed tomography, magnetic resonance imaging, optical imaging, ultrasound imaging (USI), and photoacoustic imaging. Numerous imaging agents are used while conducting medical imaging to improve the images of the inside of the body that are produced by the various imaging modalities.

Combination of different imaging techniques such as optical imaging and imaging agents such as Fluoresceine isothiocyanate (FITC) provides complementary information about an imaged target. FITC allows facile labelling of various structures and has been employed in laser-induced fluorescence detection techniques and flow cytometry of protein labelling. Further, plasmonic nanostructures (PNS) such as gold (Au), magnetoplasmonic nanostructures (MPN) based on SPION are suitable candidates for biomedical imaging and therapy. This is due to the unique optical properties of AuNPs including strong localized surface plasmon resonance (LSPR) because of adjustable nanoparticle size, shape, biocompatibility due to their inert surface, nontoxicity, and surface conjugation chemistry. Although the various imaging agents are known in the art, the difficulty lies in the delivery of the imaging agent to a specific target site.

In light of the foregoing discussion, there is a need for an improved process that enables site specific delivery of the imaging agents.

SUMMARY

A method for fabricating a nanostructure is disclosed. The method comprises adding a fungal mycelium in a growth vessel. The growth vessel comprising a growth medium. Further, the nanostructure is added in the growth vessel. The nanostructure added is absorbed and distributed throughout the fungal mycelium.

In yet another embodiment, a delivery vehicle for payload is disclosed. The delivery vehicle comprises a nanostructure fabricated within a fungal mycelium. The nanostructure is absorbed by the fungal mycelium and dispersed within hyphae of the fungal mycelium.

BRIEF DESCRIPTION OF DRAWINGS

Embodiments are illustrated by way of example and not limitation in the figures of the accompanying drawings, in which like references indicate similar elements and in which.

DETAILED DESCRIPTION

The following detailed description includes references to the accompanying drawings, which form part of the detailed description. The drawings show illustrations in accordance with example embodiments. These example embodiments are described in enough details to enable those skilled in the art to practice the present subject matter. However, it may be apparent to one with ordinary skill in the art that the present invention may be practised without these specific details. In other instances, well-known methods, procedures and components have not been described in detail so as not to unnecessarily obscure aspects of the embodiments. The embodiments can be combined, other embodiments can be utilized, or structural and logical changes can be made without departing from the scope of the invention. The following detailed description is, therefore, not to be taken as a limiting sense.

In this document, the terms "a" or "an" are used, as is common in patent documents, to include one or more than one. In this document, the term "or" is used to refer to a non-exclusive "or", such that "A or B" includes "A but not B", "B but not A", and "A and B", unless otherwise indicated.

Figure 1A:
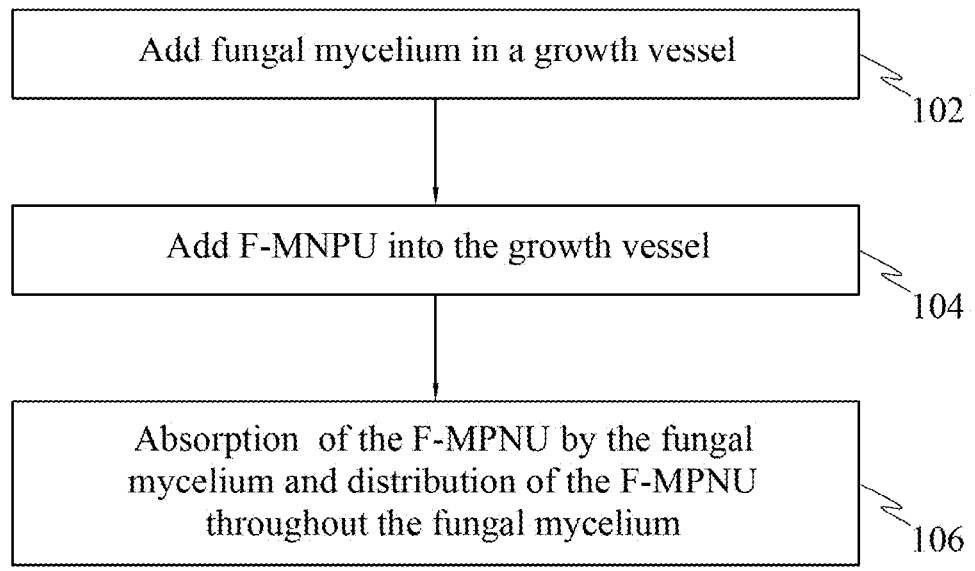
FIG. 1A is an exemplary flowchart explaining a process for fabricating fluoresceine isothiocyanate (FITC) conjugated magnetoplasmonic nanourchins (MPNU) F-MPNU within a fungal mycelium, in accordance with an embodiment.

Referring to FIG. 1A is a method for fabrication of a nanostructure. In an embodiment, the nanostructure is a fluoresceine isothiocyanate (FITC) conjugated magnetoplasmonic nanourchins (F-MPNU) 116 (shown in FIG. 2). The FITC conjugated magnetoplasmonic nanourchins 116 is fabricated within a fungal mycelium 114 (shown in FIG. 1B). The fungal mycelium may be for example but not limited to *Pleurotus eryngii* (P.e). The mycelium of the fungi *Pleurotus eryngii* (P.e) is a biocompatible and non-cytotoxic material.

Figure 1B:
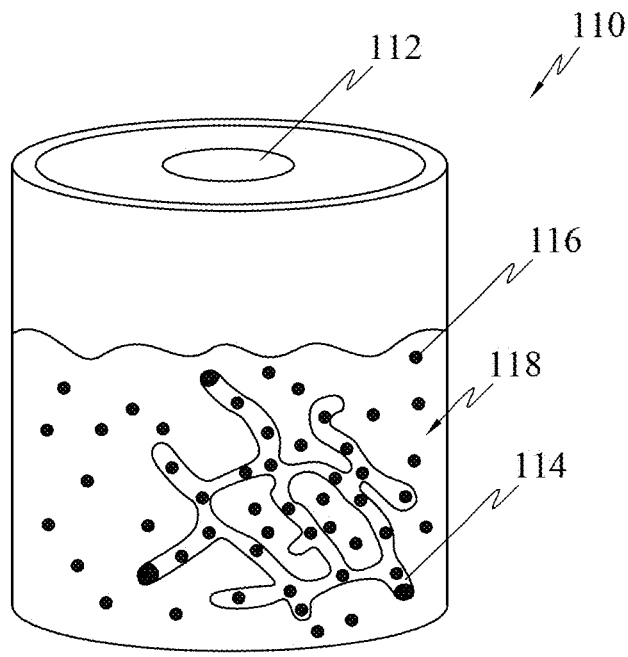
FIG. 1B exemplary illustrates a growth vessel 110 to promote the growth of fungal mycelium 114, in accordance with an embodiment.

Referring to FIG. 1B, the fabrication of the nanostructure i.e. the FITC conjugated magnetoplasmonic nanourchins 116 is carried out in a growth vessel 110. The growth vessel 110 comprises a micropore filter 112 on the top of the growth vessel 110. The micropore filter 112 allows ample exchange of gases, whereas prevents the introduction of contaminants into the growth vessel 110.

Referring back to FIG. 1A, at step 102 the fungal mycelium 114 is subjected into the growth vessel 110 (refer FIG. 1B). The growth vessel 110 comprises a growth medium 118 (shown in FIG. 1B). The growth medium 118 is for example, but not limited to, Dulbecco's Modified Eagle Medium (DMEM), a liquid culture supplemented with protein serum to promote cellular development.

Figure 2:
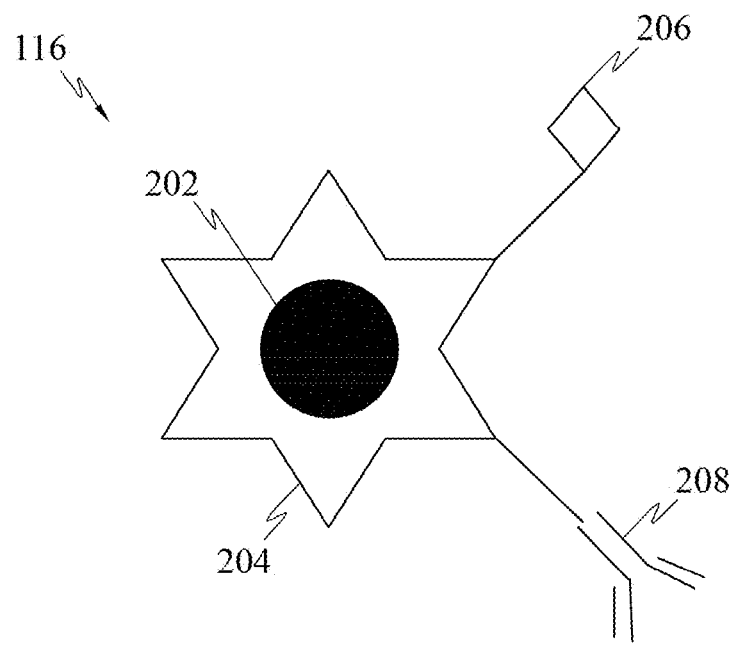
FIG. 2 illustrates the F-MPNU 116, in accordance with an embodiment.

At step 104, nanostructure in controlled amount is also added into the growth vessel 110. In an embodiment, the nanostructure is F-MPNU 116. Referring to FIG. 2, the F-MPNU 116 comprises a functionalised superparamagnetic iron oxide (SPION) 202. The SPION is synthesised by a process disclosed below which is well known in the art.

Once the SPION is synthesized, the SPION is functionalized with amino silane. In an embodiment, the amino silane is for example but not limited to 3-aminopropyltriethoxysilane (APTS). The functionalised SPION 202 is then coated with gold nanourchins 204 and further conjugated with a payload 206 and targeting agent 208. The targeting agent 208 facilitates selective targeting and cellular uptake via endocytosis process. The targeting agents 208 may be for example but not limited to a target specific antibody Ab.

SYNTHESIS OF SPIONS: A solution of $FeCl_3 \cdot 6H_2O$ (0.012 M) and $FeSO4 \cdot 7H_2O$ (0.006 M) was prepared as a source of iron ions by dissolving the respective chemicals in DI water. After addition of these solutions to each other under $N_2$ protection, the resulting solution was treated by ultrasonic wave, and then dropped into ammonia aqueous solution (0.9 M) with violently stirring, $N_2$ was used during the reaction to prevent critical oxidation. For completing coprecipitation reaction, violently stirring was continued for 1 h, and then followed for 30 min at 70° C. to modify the surface of nanoparticles. The obtained magnetite was washed immediately with water for five times and ethanol for two times by magnetic separation.

In an embodiment, the payload 206 may be an imaging agent, drug payloads or other payloads. The payload may be a drug payload if the objective is to deliver drug or bioactive agent to a specific target site (drug delivery). The drug payloads if administered in their untargeted forms are too toxic being highly active molecules.

In another embodiment, the payload 206 may be an imaging agent if the objective is to perform photothermal therapy for tumor or bioimaging. The imaging agent may be a fluoresceine isothiocyanate (FITC). The selection of the imaging agent depends on the imaging modalities selected. The payload 206 in the F-MPNU 116 is carried via the mycelial network or fungal mycelium 114, utilising the hyphae as the natural delivery and dispersion system or vehicle. The delivery of the imaging agent, results in an image being made of the target site, likewise, the delivery of the bioactive agent or drug results in a biological effect on an organ, tissue, cell, or cell type i.e. on the target site.

At step 106, the fungal mycelium 114 introduced into the growth vessel 110 will consume and disperse the F-MPNU 116 throughout its mycelial networks, thereby creating a natural means of achieving a wide distribution of nanostructure throughout the growth area. The process of active uptake of the F-MPNU 116 occurs as the fungi (organism) interacts with its environment by way of extracellular digestion. The F-MPNU 116 are consumed along with nutrients through active diffusion process and distributed throughout the fungi via nutrient flow.

After the growth and distribution phase, the tagged nanostructures i.e., the F-MPNU 116 are released from the fungal mycelium 114 using an internal or external stimulus. Once the mycelium complex comprising the nanostructure is taken by tissue matrix or cells either by passive (i.e., diffusion) or active (i.e., targeted) method, the mycelia network begins to grow until the optimum day, after which it is disintegrated. The disintegration may occur due to internal stimulus. The internal stimulus may be for example, but not limited to, temperature and pH. Alternatively, the disintegration may occur by application of external stimulus, for example, but not limited to, application of laser. After the disintegration of the F-MPNU 116 from the fungal mycelium 114, the F-MPNU is distributed uniformly throughout the tissue and ready for imaging or photothermal therapy.

Figure 3:
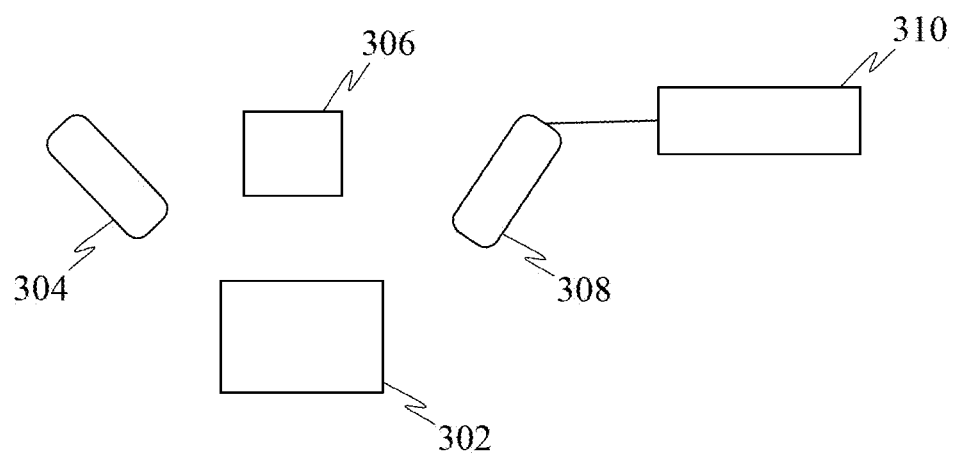
FIG. 3 illustrates irradiating a target sample 302, in accordance with an embodiment.

Referring to FIG. 3, the target sample 302 is subjected to a near infrared diode laser 304 at 808 nm. The imaging agent 206 for example FITC is visible as green light when observed under a fluorescence microscope 306. As the target sample 302 is irradiated, plasmonic nanoparticles (PNP), such as gold nanourchins, interacts with the electromagnetic wave. Such interaction of the gold nanourchins with the conduction band electrons are excited leading to a coherent oscillation, which exhibits strong optical absorption and scattering due to localized surface plasmon resonance (LSPR). As a result of plasmon oscillation, a dipole is induced, which enhances the local electric field at the surface of PNP, and hence, a strong light absorption and scattering occurs at the surface plasmon resonance (SPR) frequency, which is also temperature-dependent. The absorbance and scattering cross sections describe the intensity of absorbed or scattered light at a given frequency. The heat produced by the PNP is due to the absorption of incident photons and conversion of photon energy into heat energy, and eventually is transferred to the surrounding matrix. The laser heat induced by the F-MNPU 116 is detected by an infrared camera 308 which is further connected to a monitor 310 for further analysis.

In an embodiment, the nanostructure i.e. F-MPNU 116 fabricated within the fungal mycelium 114 may be used as the delivery vehicle to deliver the payload 206 to a target site or target cell of a subject. The payload 206 may be delivered to a target specific site as the targeting agent 208 is attached to the gold nanourchins 204 that enables site specific delivery of the payload 206. The use of such delivery vehicle has certain advantages such as, the gold nanourchins have sharp tips which enhances the photothermal effect due to the magnification of electromagnetic field, the superparamagnetic nanoparticles (SPION) core provides the possibility of nanostructures manipulation under external magnetic field if desired, and the use of a specific antibody (Ab) enables for selective targeting.

The delivery vehicle comprising the fungal mycelium 114 and the F-MPNU has various biomedical applications such as bioimaging, photothermal therapy of tumor and drug delivery based on the uniform distribution of the content. The main advantages of the delivery vehicle includes penetration of the fungal mycelium network within tissue and at cellular level and more uniform distribution of the nanostructures within the tissue particularly in the case of localized injection, where the nanostructures can be concentrated non-uniformly at one position, which would affect the quality of photothermal therapy and imaging.

It shall be noted that the processes described above are described as sequence of steps; this was done solely for the sake of illustration. Accordingly, it is contemplated that some steps may be added, some steps may be omitted, the order of the steps may be re-arranged, or some steps may be performed simultaneously.

Many alterations and modifications of the present invention will no doubt become apparent to a person of ordinary skill in the art after having read the foregoing description. It is to be understood that the phraseology or terminology employed herein is for the purpose of description and not of limitation. It is to be understood that the description above contains many specifications; these should not be construed as limiting the scope of the invention but as merely providing illustrations of some of the personally preferred embodiments of this invention. Thus, the scope of the invention should be determined by the appended claims and their legal equivalents rather than by the examples given.

What is claimed is:

1. A method for fabricating a nanostructure delivery vehicle, the method comprising:

providing a fungal mycelium in a growth vessel, wherein the growth vessel comprises a growth medium;

providing a nanostructure in the growth vessel;

permitting the nanostructure to be uptaken and distributed in the fungal mycelium during growth of the fungal mycelium.

2. The method according to claim 1, wherein the nanostructure comprises a fluoresceine isothiocyanate (FITC)-conjugated magnetoplasmonic nanourchin (MPNU).

3. The method according to claim 2, wherein the FITC-conjugated MPNU comprises:

a functionalised superparamagnetic iron oxide (SPION) core;

a coating of gold nanourchins on the functionalised SPION core; and a payload comprising FITC attached to the gold nanourchins.

4. The method according to claim 3, wherein a targeting agent is attached to the gold nanourchins.

5. The method according to claim 4, wherein the targeting agent is a target specific antibody.

6. The method according to claim 1, wherein the nanostructure comprises a payload, the payload comprising a drug payload or an imaging agent.

7. The method according to claim 3, wherein the SPION core is functionalized with 3-aminopropyltriethoxysilane (APTS).

8. The method according to claim 1, wherein the fungi mycelium is *Pleurotus eryngii*.

9. The method according to claim 1, further comprising:

introducing the fungal mycelium comprising the nanostructure to a tissue matrix or cells at a target site; and disintegrating or releasing the nanostructure from the fungal mycelium by application of internal stimulus or external stimulus.

10. The method according to claim 1, wherein the method further comprises subjecting the fungal mycelium comprising the nanostructure to energy in an amount sufficient to disintegrate the nanostructure from the fungal mycelium.

11. The method according to claim 1, wherein the nanostructure comprises either a payload and/or a targeting agent.

12. The method according to claim 11, wherein the nanostructure comprises both a payload and a targeting agent.

13. The method according to claim 11, wherein the nanostructure comprises a payload, and the payload comprises an imaging agent and/or a bioactive agent.

14. The method according to claim 13, wherein the payload comprises a bioactive agent, and the bioactive agent comprises a drug.

15. The method according to claim 13, wherein the payload comprises an imaging agent.

* * * * *